US 11,980,717 B1

United States Patent
Garrison (10) Patent No.: US 11,980,717 B1
(45) Date of Patent: May 14, 2024

(54) MIXTURES INCLUDING NITROUS OXIDE

(71) Applicant: Thomas E. Garrison, Scottsdale, AZ (US)

(72) Inventor: Thomas E. Garrison, Scottsdale, AZ (US)

( * ) Notice: Subject to any disclaimer, the term of this patent is extended or adjusted under 35 U.S.C. 154(b) by 0 days.

(21) Appl. No.: 18/104,540

(22) Filed: Feb. 1, 2023

(51) Int. Cl.
*A61K 33/00* (2006.01)
*A61K 45/06* (2006.01)
*A61M 11/00* (2006.01)
*A61M 16/06* (2006.01)

(52) U.S. Cl.
CPC ............. *A61M 16/06* (2013.01); *A61K 33/00* (2013.01); *A61K 45/06* (2013.01); *A61M 11/00* (2013.01)

(58) Field of Classification Search
CPC ........... C01B 21/22; A61M 2202/0283; A61M 16/104; A61M 16/12; A61M 16/009; A61M 16/0093; A61M 16/0891; A61M 16/06; A61M 11/04; A61M 11/041; A61M 11/042; A61M 11/02; A61M 11/005; Y02C 20/10
See application file for complete search history.

(56) References Cited

U.S. PATENT DOCUMENTS

| | | | |
|---|---|---|---|
| 6,125,844 A * | 10/2000 | Samiotes | A61M 15/0065 128/200.23 |
| 6,221,377 B1 | 4/2001 | Meyer | |
| 9,757,528 B2 | 9/2017 | Rubin | |
| 11,065,223 B2 | 7/2021 | Rosenblatt et al. | |
| 2008/0066741 A1* | 3/2008 | LeMahieu | A61M 16/0069 128/200.14 |
| 2010/0163033 A1* | 7/2010 | Hyde | A61B 5/4833 128/203.14 |
| 2012/0045528 A1 | 2/2012 | Bessiere et al. | |
| 2019/0126096 A1* | 5/2019 | Squibb | A62B 25/005 |
| 2019/0328699 A1* | 10/2019 | Forde | A61M 16/14 |
| 2023/0001128 A1* | 1/2023 | Shuster | A61M 11/042 |

FOREIGN PATENT DOCUMENTS

| | | | |
|---|---|---|---|
| CN | 103127165 A | * | 6/2013 |
| WO | 2021138602 A1 | | 7/2021 |
| WO | WO-2022069690 A2 | * | 4/2022 |

OTHER PUBLICATIONS

Jonathan Jarry, "This Sticky Pain Patch's Science Hits a Sticky Patch", Sep. 23, 2022, McGill University, All Pages (Year: 2022).*
2021Review.com, "Kailo Review: Targeted Pain Relief Patch Nanotech That Works—2021 Review", Mar. 11, 2021, GlobeNewswire, All Pages (Year: 2021).*

(Continued)

*Primary Examiner* — Joseph D. Boecker
*Assistant Examiner* — Brian T Khong
(74) *Attorney, Agent, or Firm* — Kunzler Bean & Adamson (57) ABSTRACT

Apparatus for providing a mixture including nitrous oxide ($N_2O$) to a subject are disclosed. One apparatus includes at least one reservoir storing at least $N_2O$ and a delivery mechanism in communication with each reservoir. The delivery mechanism is configured to introduce a mixture including $N_2O$ and at least a first additive combined with the $N_2O$ to one of a mouth of a subject, a nose of the subject, or both the mouth and the nose of the subject for inhalation by the subject.

20 Claims, 6 Drawing Sheets

(56) References Cited

OTHER PUBLICATIONS

English Machine Translation of CN-103127165-A provided by Espacenet (Year: 2013).*

Kalmoe et al., "Ketamine and nitrous oxide: The evolution of NMDA receptor antagonists as antidepressant agents", Mar. 14, 2020, Elsevier, All Pages (Year: 2020).*

PCT/US2023/012117, "Notification of Transmittal of the International Search Report and Written Opinion of the International Searching Authority, or the Declaration", International Searching Authority, Apr. 13, 2023, pp. 1-13.

* cited by examiner

MIXTURES INCLUDING NITROUS OXIDE

FIELD

The subject matter disclosed herein relates to nitrous oxide ($N_2O$) and, more particularly, relates to mixtures that include $N_2O$.

BACKGROUND

Nitrous oxide ($N_2O$) is used in medicine and dentistry and is often referred to as laughing gas. However, $N_2O$ is typically used singularly or alone, which can limit the usefulness of $N_2O$.

BRIEF SUMMARY

The subject matter of the present disclosure provides examples of mixtures that include nitrous oxide ($N_2O$) that can increase the usefulness of $N_2O$. Accordingly, the subject matter of the present application has been developed in response to the present state of the art, and in particular, in response to the limited uses of $N_2O$ and/or the limited uses of conventional apparatus (and/or systems) and methods that use $N_2O$.

Disclosed herein is an apparatus for providing a mixture including nitrous oxide ($N_2O$) to a subject. The apparatus includes at least one reservoir storing at least $N_2O$ and a delivery mechanism in communication with each reservoir. The delivery mechanism is configured to introduce a mixture including $N_2O$ and at least a first additive combined with the $N_2O$ to one of a mouth of a subject, a nose of the subject, or both the mouth and the nose of the subject for inhalation by the subject. The preceding subject matter of this paragraph characterizes example 1 of the present disclosure.

The mixture comprises one of a liquid, a gas, and a compressed gas. The preceding subject matter of this paragraph characterizes example 2 of the present disclosure, wherein example 2 also includes the subject matter according to example 1, above.

The mixture comprises a first predetermined percentage of the $N_2O$ in the range of 20% to 99%. The preceding subject matter of this paragraph characterizes example 3 of the present disclosure, wherein example 3 also includes the subject matter according to example 1, above.

The mixture comprises a second predetermined percentage of the first additive in the range of 1% to 80%. The preceding subject matter of this paragraph characterizes example 4 of the present disclosure, wherein example 4 also includes the subject matter according to any one of examples 1 or 3, above.

The first predetermined percentage and the second predetermined percentage total one of 100% of the mixture and less than 100% of the mixture. The preceding subject matter of this paragraph characterizes example 5 of the present disclosure, wherein example 5 also includes the subject matter according to any one of examples 1, 3, or 4, above.

The mixture comprises a predetermined percentage of the first additive in the range of 1% to 80%. The preceding subject matter of this paragraph characterizes example 6 of the present disclosure, wherein example 6 also includes the subject matter according to example 1, above.

The mixture comprises a second additive combined with the $N_2O$ and the first additive. The preceding subject matter of this paragraph characterizes example 7 of the present disclosure, wherein example 7 also includes the subject matter according to example 1, above.

The mixture comprises at least 20% of the $N_2O$. The preceding subject matter of this paragraph characterizes example 8 of the present disclosure, wherein example 8 also includes the subject matter according to any one of examples 1 or 7, above.

The first additive comprises one of compressed air, pure oxygen ($O_2$), air, and atmospheric air. The preceding subject matter of this paragraph characterizes example 9 of the present disclosure, wherein example 9 also includes the subject matter according to example 1, above.

The first additive comprises a cannabis extract. The preceding subject matter of this paragraph characterizes example 10 of the present disclosure, wherein example 10 also includes the subject matter according to example 1, above.

The first additive comprises one of an essential oil, an herbal extract, a supplement, a medication, a vitamin, and a nutrient. The preceding subject matter of this paragraph characterizes example 11 of the present disclosure, wherein example 11 also includes the subject matter according to example 1, above.

The first additive comprises the essential oil and the essential oil comprises one of lemon oil, peppermint oil, lavender oil, tee tree oil, eucalyptus oil, clove oil, chamomile oil, orange oil, spearmint oil, rosemary oil, grapefruit oil, oregano oil, ginger oil, lemongrass oil, spruce oil, pine oil, sandalwood oil, cedarwood oil, marjoram oil, clary sage oil, valerian oil, patchouli oil, vetiver oil, ylang ylang oil, frankincense oil, myrrh oil, neroli oil, and bergamot oil. The preceding subject matter of this paragraph characterizes example 12 of the present disclosure, wherein example 12 also includes the subject matter according to any one of examples 1 or 11, above.

The first additive comprises caffeine. The preceding subject matter of this paragraph characterizes example 13 of the present disclosure, wherein example 13 also includes the subject matter according to example 1, above.

The first additive comprises a silver. The preceding subject matter of this paragraph characterizes example 14 of the present disclosure, wherein example 14 also includes the subject matter according to example 1, above.

The silver comprises one of a colloidal silver and a nano-silver. The preceding subject matter of this paragraph characterizes example 15 of the present disclosure, wherein example 15 also includes the subject matter according to any one of examples 1 or 14, above.

The first additive comprises a nano-capacitor. The preceding subject matter of this paragraph characterizes example 16 of the present disclosure, wherein example 16 also includes the subject matter according to example 1, above.

The first additive comprises one or more flavorings and at least one of the one or more flavorings comprises a fruit flavoring, a mint flavoring, and a vanilla flavoring. The preceding subject matter of this paragraph characterizes example 17 of the present disclosure, wherein example 17 also includes the subject matter according to example 1, above.

The mixture comprises one of a single-use quantity and a multi-use quantity. The preceding subject matter of this paragraph characterizes example 18 of the present disclosure, wherein example 18 also includes the subject matter according to example 1, above.

The at least one reservoir comprises a reservoir storing the mixture of the N2O and the first additive. The preceding subject matter of this paragraph characterizes example 19 of the present disclosure, wherein example 19 also includes the subject matter according to example 1, above.

The at least one reservoir comprises at least a first reservoir storing the $N_2O$ and a second reservoir storing the first additive. The preceding subject matter of this paragraph characterizes example 20 of the present disclosure, wherein example 20 also includes the subject matter according to example 1, above.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Various embodiments disclosed herein provide mixtures that include nitrous oxide ($N_2O$). Various other embodiments provide apparatus and methods that use $N_2O$.

It has been discovered that $N_2O$ is a non-competitive channel blocker of N-methyl-D-aspartate (NMDA) receptors and includes effects similar to the known NMDA receptor effects of Ketamine without the addictive shortcomings of Ketamine. That is, it has been discovered that inhaling a dose of $N_2O$ can produce a relatively rapid and relatively long-lasting anti-depressant effect, anti-anxiety effect on a subject with limited and/or reduced addictive consequences. Additionally, a dose of $N_2O$ may slow down the effects of Alzheimer's disease, memory loss, and/or brain damage. Further $N_2O$ can improve one or more symptoms of post-traumatic stress disorder (PTSD) by blocking induction and expression of behavioral sensitization by stress and/or blocking cross-sensitization between stress and stimulants. Further, $N_2O$ can positively affect the hyperactivity or hypofunction of the NMDA pathway and/or pathophysiology of a subject, which can at least decrease/reduce the effects of ischemic brain injury, chronic neurodegenerative diseases, pain, depression, and/or schizophrenia.

Additionally, Ketamine use for one or more of the indications discussed above is administered intravenously (IV), and excessive dosing of Ketamine can be fatal. As such, Ketamine is currently a schedule III drug controlled by the United States Food and Drug Administration and intravenous administration of Ketamine requires that medical personnel be immediately available to perform lifesaving resuscitation should such a need arise during administration. In other words, Ketamine is not self-administered, and self-administration is not allowed by the United States Food and Drug Administration.

In contrast, $N_2O$ is not a controlled substance and can be safely and effectively self-administered. Nitrous oxide can be inhaled and does not require IV administration. That is, $N_2O$ has a better safety profile than Ketamine and does not require medical supervision during administration. With the proper amount of oxygen, which can be provided as an additive, the potential of overdosing on $N_2O$ is at least significantly reduced, if not essentially eliminated. The methodology disclosed herein provides the medical benefits of the NMDA pathway of a subject via a safe delivery method of $N_2O$ that is appropriate for non-medical environments and self-administration.

Figure 1:
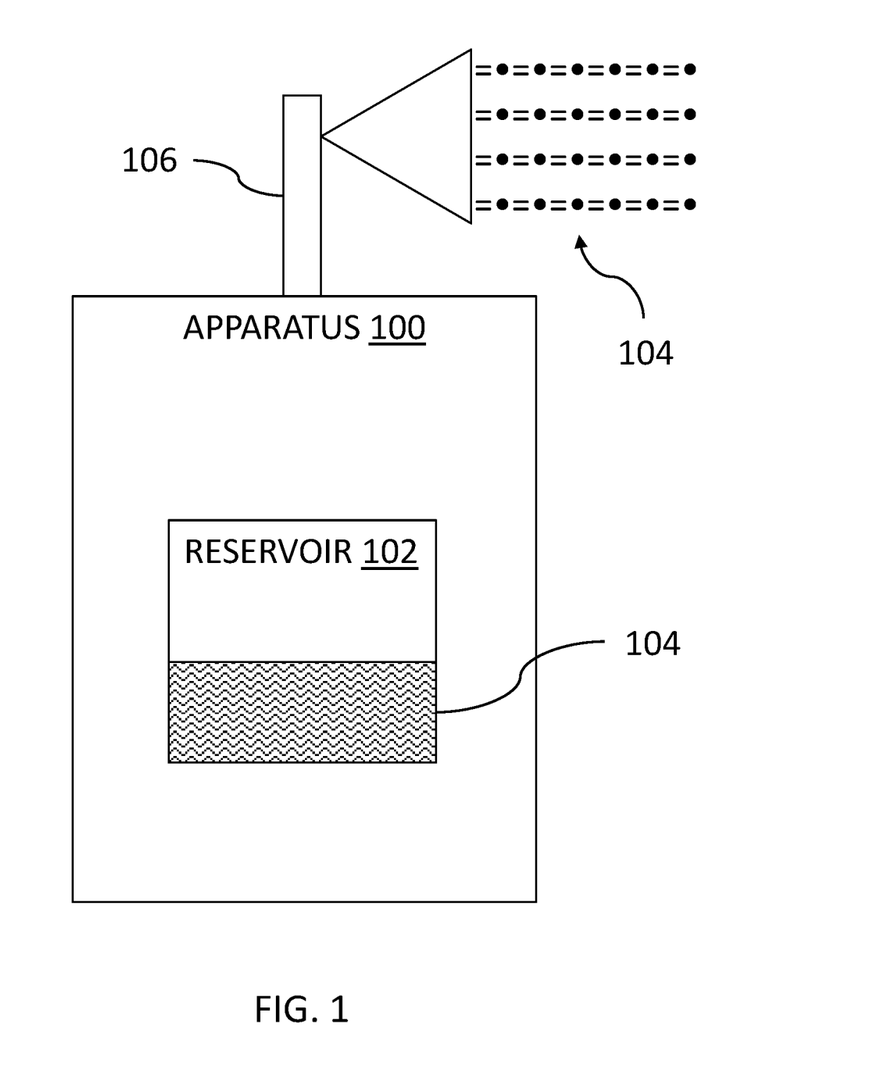
FIG. 1 is a schematic diagram of one embodiment of an apparatus including a reservoir that can provide a mixture including nitrous oxide ($N_2O$) to a subject/user.

With reference to the drawings, FIG. 1 is a diagram of one embodiment of an apparatus 100 that can provide a mixture including $N_2O$ to a subject (e.g., a human, an animal, etc.). The apparatus 100 may include any suitable device and/or system that is capable of introducing its contents (e.g., a mixture including $N_2O$) to the nose and/or mouth of a subject. Examples of an apparatus 100 include, but are not limited to, a nebulizer, an atomizer, an inhaler, a vaporizer, a humidifier, a mask, a mister, a fogger, and/or a sprayer, etc., among other devices and/or systems that are possible, each of which is contemplated herein.

At least in the exemplary embodiment shown in FIG. 1, the apparatus 100 includes, among other components, a reservoir 102 storing and/or capable of storing a mixture 104 and a delivery mechanism 106 in communication with the reservoir 102 and configured for introducing the mixture 104 to the nose and/or mouth of a subject. The reservoir 102 may include any suitable reservoir and/or type of reservoir that is known or developed in the future that is capable of storing and/or housing a mixture 104. In various embodiments, the reservoir 102 is capable of storing/housing the mixture 104 in the form of a liquid (e.g., a compressed liquid and/or a pressurized liquid) and/or a gas (e.g., a compressed gas and/or a pressurized gas).

The amount of the mixture 104 stored in the reservoir 102 may include any suitable amount of the mixture 104 that is capable of temporarily improving the psychological and/or mental health of a subject, as discussed in greater detail elsewhere herein. In some embodiments, the reservoir 102 includes a size that is capable of storing an amount of the mixture 104 defining a single dose and/or use of the mixture 104. In alternative embodiments, the reservoir 102 includes a size that is capable of storing an amount of the mixture 104 defining multiple (e.g., two or more) doses and/or uses of the mixture 104, which can include any suitable quantity of does/uses that is known or developed in the future.

The mixture 104, in various embodiments, includes $N_2O$. The amount and/or percentage of $N_2O$ in the mixture 104 may include any suitable amount and/or percentage of $N_2O$ that, subsequent to inhaling the mixture 104, is capable of at least temporarily improving the psychological and/or mental health of a subject, as discussed elsewhere herein.

In various embodiments, the mixture 104 includes at least twenty percent (20%) $N_2O$. As such, various embodiments of the mixture 104 can include an amount of $N_2O$ in the range of about 20% to about ninety-nine percent (99%) inclusive, among other amounts and/or percentages that are less than about 20% $N_2O$ or greater than about 99% $N_2O$ that are possible, each of which is contemplated herein.

The $N_2O$ in the mixture 104 may include any suitable form that is known or developed in the future. In various embodiments, the $N_2O$ in the mixture 104 may include $N_2O$ in liquid form (e.g., a compressed and/or pressurized) and/or in gas form (e.g., a compressed and/or pressurized). Further, it has been discovered that combining $N_2O$ with one or more additives to form a mixture 104 and inhaling such mixture 104 can provide additional benefits to a subject compared to $N_2O$ alone.

In further embodiments, the mixture 104 includes one or more additives combined with $N_2O$. The quantity of additives can include any suitable quantity of additives that is/are known or developed in the future. In some embodiments, the mixture 104 includes $N_2O$ combined with a single additive. In additional or alternative embodiments, the mixture 104 includes $N_2O$ combined with a plurality of additives (e.g., two (2) additives, three (3) additives, four (4) additives, five (5) additives, "n" additives, etc.).

An additive can include any suitable substance, liquid, and/or gas that can be suitably combined with $N_2O$ to form a mixture 104. Example additives can include, but are not limited to, air (e.g., pressurized air, compressed air, atmospheric air, etc.), pure oxygen ($O_2$), a cannabis extract, an essential oil, a silver and/or silver compound, an herb and/or herbal extract, a supplement, a medication, a vitamin, a nutrient, caffeine, a nano-capacitor, water ($H_2O$), hydrogen peroxide ($H_2O_2$), and/or a flavoring, etc., among other suitable additives that are possible, each of which is contemplated herein.

A cannabis extract can include any suitable substance that is known or developed in the future capable of being extracted from a cannabis plant (e.g., *Cannabis sativa*) that can be suitably combined with $N_2O$ to form a mixture 104. Example cannabis extracts can include, but are not limited to, a cannabidiol (CBD) extract and/or a tetrahydrocannabinol (THC) extract, etc., among other suitable extract from a cannabis plant that are possible, each of which is contemplated herein. In various embodiments, the mixture 104 includes $N_2O$ combined with one or more cannabis extracts or $N_2O$ combined with one or more cannabis extracts and one or more other additives.

An essential oil can include any suitable essential oil and/or combination of essential oils that is/are known or developed in the future that can be suitably combined with $N_2O$ to form a mixture 104. Example essential oils include, but are not limited to, lemon oil, peppermint oil, lavender oil, tee tree oil, eucalyptus oil, clove oil, chamomile oil, orange oil, spearmint oil, rosemary oil, grapefruit oil, oregano oil, ginger oil, lemongrass oil, spruce oil, pine oil, sandalwood oil, cedarwood oil, marjoram oil, clary sage oil, valerian oil, patchouli oil, vetiver oil, ylang ylang oil, frankincense oil, myrrh oil, neroli oil, and/or bergamot oil, among other suitable essential oils that are possible, each of which is contemplated herein. In various embodiments, the mixture 104 includes $N_2O$ combined with one or more essential oils or $N_2O$ combined with one or more essential oils and one or more other additives. A silver may include any suitable silver and/or silver compound that is known or developed in the future that can be suitably combined with $N_2O$ to form a mixture 104. Example silvers may include, but are not limited to, a colloidal silver, nano-silver, silver oxide ($Ag_2O$), etc., among other suitable silvers and/or silver compounds that are possible, each of which is contemplated herein. In some embodiments, a silver can include a colloidal silver and/or nano-silver manufactured by SilverCeuticals® LLC of Lindon, Utah. In various embodiments, the mixture 104 includes one or more silvers combined with at least $N_2O$.

An herb and/or herbal extract may include any suitable herb and/or extract from any suitable herb that is known or developed in the future that can be suitably combined with $N_2O$ to form a mixture 104. Example herbs and/or extracts from a herb can include, but are not limited to, echinacea, ginseng, Siberian, ginseng, *Ginkgo biloba*, elderberry, St. John's wort, turmeric, ginger, valerian, chamomile, mint, clover, henbane, mistletoe, monkshood, pasqueflower, primrose, vervain, garlic, saw palmetto, goldenseal, aloe, tulsi, amla, ashwagandha, gotu kola, neem, cumin, peppermint, and/or cinnamon, etc., among other herbs and/or herbal extracts that are possible, each of which is contemplated herein. In various embodiments, the mixture 104 includes one or more herbs and/or one or more herbal extracts combined with at least $N_2O$.

A supplement may include any suitable supplement that is known or developed in the future that can be suitably combined with $N_2O$ to form a mixture 104. Example supplements can include, but are not limited to, fish oil, a probiotic, Omega-3, curcumin, collagen, CoQ10, chondroitin, coconut oil, rose hips, melatonin, apple cider vinegar, green tea and/or green tea extract, cocoa and/or cocoa extract, and/or dark chocolate and/or dark chocolate extract, etc., among other supplements that are possible, each of which is contemplated herein. In various embodiments, the mixture 104 includes one or more supplements combined with at least $N_2O$.

A medication may include any suitable medication that is known or developed in the future that can be suitably combined with $N_2O$ to form a mixture 104. In various embodiments, a medication includes any medication that can be effectively absorbed through the lungs, without notably toxicity, and that can include a beneficial (perceived and/or substantiated) effect on the body of a subject (e.g., human, animal, etc.). Example medications can include, but are not limited to, a medication for asthma, chronic obstructive pulmonary disease (COPD), an infection, inflammation, cystic fibrosis, and/or an autoimmune disease, etc., among other medications that are possible, each of which is contemplated herein.

A vitamin may include any suitable vitamin or multivitamin that is known or developed in the future that can be suitably combined with $N_2O$ to form a mixture 104. Example vitamins include, but are not limited to, Vitamin A, Vitamin B (e.g., Vitamin B1 (Thiamine), Vitamin B2 (Riboflavin), Vitamin B3 (Niacin), Vitamin B5 (Pantothenic Acid), Vitamin B6 (Pyridoxine), Vitamin B7 (Biotin), Vitamin B9 (Folate or Folic Acid), Vitamin B12 (Cobalamin), a B-complex, etc.), Vitamin C (Ascorbic Acid), Vitamin D, Vitamin E, Vitamin K, and/or Choline, etc., among other vitamins and/or multivitamins that are possible, each of which is contemplated herein. In various embodiments, the mixture 104 includes one or more vitamins and/or a multivitamin combined with at least $N_2O$.

A nutrient may include any suitable nutrient and/or mineral that is known or developed in the future that can be suitably combined with $N_2O$ to form a mixture 104. Example nutrients include, but are not limited to, Calcium, Chloride, Chromium, Copper, Fluoride, Iodine, Iron, Magnesium, Manganese, Molybdenum, Phosphorus, Potassium, Selenium, Sodium, and/or Zinc, etc., among other nutrients and/or minerals that are possible, each of which is contemplated herein. In various embodiments, the mixture 104 includes one or more nutrients and/or minerals combined with at least $N_2O$.

A flavoring may include any suitable flavoring that is known or developed in the future that can be suitably combined with $N_2O$ to form a mixture 104. Example flavorings include, but are not limited to, a fruit flavoring (e.g., apple, strawberry, raspberry, pear, blackberry, blueberry, peach, plum, apricot, banana, pineapple, watermelon, grape, cherry, mango, papaya, kiwi, cantaloupe, orange, clementine, lemon, grapefruit, and/or lime, etc.), a mint flavoring (e.g., spearmint, peppermint, etc.), a chocolate flavoring, a coffee flavoring, and/or a vanilla flavoring, etc., among other flavorings that are possible, each of which is contemplated herein. In various embodiments, the mixture 104 includes one or more flavorings combined with at least $N_2O$.

A nano-capacitor may include any suitable nano-capacitor and/or type of nano-capacitor that is known or developed in the future. In some embodiments, the nano-capacitor includes a nano-capacitor manufactured by nCAP® Technologies LLC of Heber City, Utah.

The additive(s) in the mixture 104 may include any suitable form that is known or developed in the future. In various embodiments, the additive(s) in the mixture 104 may include one or more additives in a liquid form and/or one or more additives in a gas/gaseous form.

In various embodiments, the mixture 104 includes a minimum of about one percent (1%) of the one or more additives. As such, various embodiments of the mixture 104 can include an amount of the additive(s) in the range of about 1% to about eighty percent (80%) inclusive, among other amounts and/or percentages that are less than about 1% of the additive(s) or greater than about 80% of the additive(s) that are possible, each of which is contemplated herein.

In some embodiments, the $N_2O$ and the additive(s) make up the entirety (e.g., one hundred percent (100%)) or the substantial entirety of the mixture 104. In other embodiments, the $N_2O$ and the additive(s) make up less than 100% of the mixture 104.

A delivery mechanism 106 may include any suitable device and/or system that is capable of introducing a mixture 104 stored/housed in a reservoir 102 of an apparatus 100 to the nose and/or mouth of a subject. Examples of a delivery mechanism 106 can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 106 are configured to emit and/or expel the mixture 104 in the form of a spray, a fine spray, a mist, a stream, a vapor, an aerosol, a sprinkle, droplets, and/or a fog, etc., among other forms that are capable of being inhaled by a subject that are possible, each of which is contemplated herein.

Since the mixture 104 includes a combination of $N_2O$ and one or more additives, the delivery mechanism 106, in some embodiments, is configured to simultaneously deliver the $N_2O$ and the one or more additives to the mouth of a subject (e.g., a user) for inhalation by the subject/user. Similarly, since the mixture 104 includes a combination of $N_2O$ and one or more additives, the delivery mechanism 106, in some embodiments, is configured to simultaneously deliver the $N_2O$ and the one or more additives to the nose of a subject/user for inhalation by the subject/user. Similar still, since the mixture 104 includes a combination of $N_2O$ and one or more additives, the delivery mechanism 106, in some embodiments, is configured to simultaneously deliver the $N_2O$ and the one or more additives to both the mouth and the nose of a subject/user for inhalation by the subject/user.

FIGS. 2A through 2D are schematic diagrams of various embodiments of an apparatus 200A, 200B, 200C, and 200D that can provide a mixture 204A, 204B, 204C, and 204n, respectively (hereinafter referred to singularly and/or collectively simply as mixture(s) 204), including $N_2O$ to a subject and/or user similar to the apparatus 100 discussed with reference to FIG. 1. At least in the embodiment illustrated in FIG. 2A, the apparatus 200A includes, among other components, a reservoir 208 configured to store and/or storing $N_2O$ 210, a reservoir 212A configured to store and/or storing a first additive 214A, and a delivery mechanism 206A in communication with the reservoirs 208 and 212A and configured for introducing a mixture 204A to the nose and/or mouth of a subject.

Figure 2A:
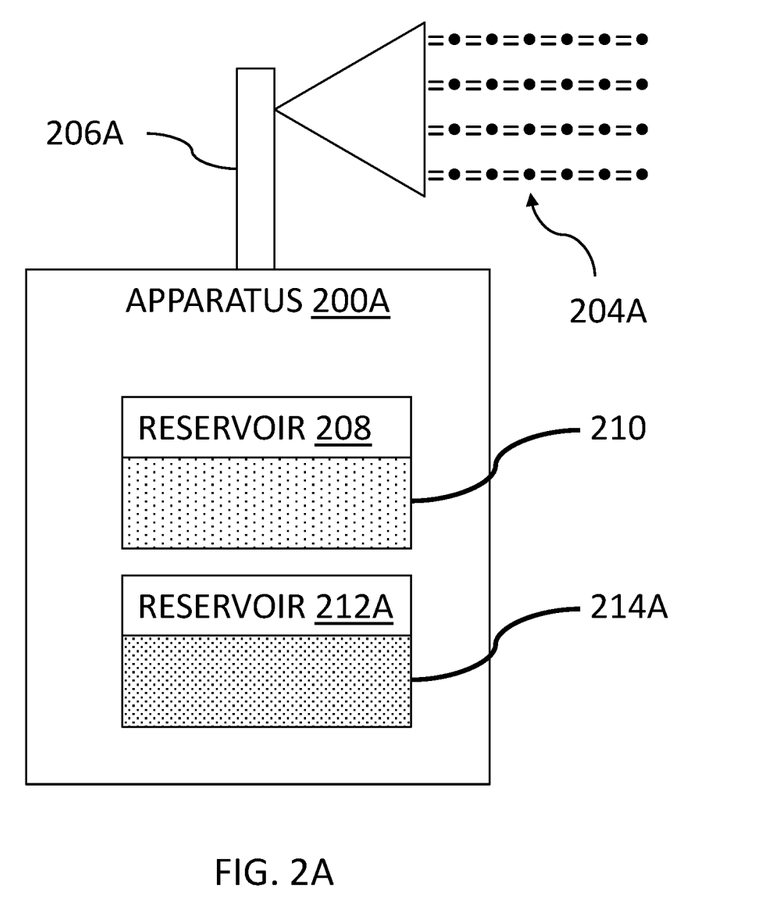
FIGS. 2A through 2D are schematic diagrams of various other embodiments of an apparatus that can provide a mixture including $N_2O$ to a subject/user.

A reservoir 208 may include any suitable reservoir and/or type of reservoir that is known or developed in the future that is capable of storing and/or housing an amount of $N_2O$ 210. In various embodiments, the reservoir 208 is capable of storing/housing the $N_2O$ 210 in the form of a compressed and/or pressurized liquid and/or a compressed and/or pressurized gas. As such, the $N_2O$ 210 stored in the reservoir 208 may be in the form of compressed liquid $N_2O$, pressurized liquid $N_2O$, compressed gaseous $N_2O$, and/or pressurized gaseous $N_2O$.

A reservoir 212A may include any suitable reservoir and/or type of reservoir that is known or developed in the future that is capable of storing and/or housing an amount of a first additive 214A. In various embodiments, the reservoir 212A is capable of storing/housing the first additive 214A in the form of a compressed and/or pressurized liquid and/or a compressed and/or pressurized gas. As such, the first additive 214A stored in the reservoir 212A may be in the form of a compressed liquid, a pressurized liquid, a compressed gas, and/or a pressurized gas.

The first additive 214A can include any suitable additive, substance, liquid, and/or gas that can be suitably combined with the $N_2O$ 210 to form a mixture 204A similar to at least one embodiment of the mixture 104 discussed above with reference to FIG. 1. For example, the first additive 214A may include, but is not limited to, air, pure oxygen, a cannabis extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206A may include any suitable device and/or system that is capable of introducing a mixture 204A including $N_2O$ 210 and the first additive 214A to the nose and/or mouth of a subject and/or user similar to the delivery mechanism 106 discussed above with reference to FIG. 1. Examples of a delivery mechanism 206A can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206A are configured to emit and/or expel the mixture 104 in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206A is configured to combine and/or facilitate combining the $N_2O$ 210 stored/housed in the reservoir 208 and the first additive 214A stored/housed in the reservoir 212A to generate and/or facilitate generating the mixture 204A. Since the mixture 204A includes a combination of the $N_2O$ 210 and the first additive 214A, the delivery mechanism 206A, in some embodiments, is configured to simultaneously deliver the $N_2O$ 210 and the first additive 214A to the mouth and/or nose of the subject and/or user for inhalation by the subject/user.

In various embodiments, the mixture 204A includes at least 20% of the $N_2O$ 210. That is, various embodiments of the mixture 204A can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204A, in various embodiments, includes a minimum of about 1% of the first additive 214A. That is, various embodiments of the mixture 204A can include an amount of the first additive 214A in the range of about 1% to about 80% inclusive, among other amounts and/or percentages that are less than about 1% of the first additive 214A or greater than about 80% of the first additive 214A that are possible, each of which is contemplated herein.

In some embodiments, the $N_2O$ 210 and the first additive 214A make up the entirety or substantially the entirety of the mixture 204A. In other embodiments, the $N_2O$ 210 and the first additive 214A make up less than 100% of the mixture 204A.

Figure 2B:
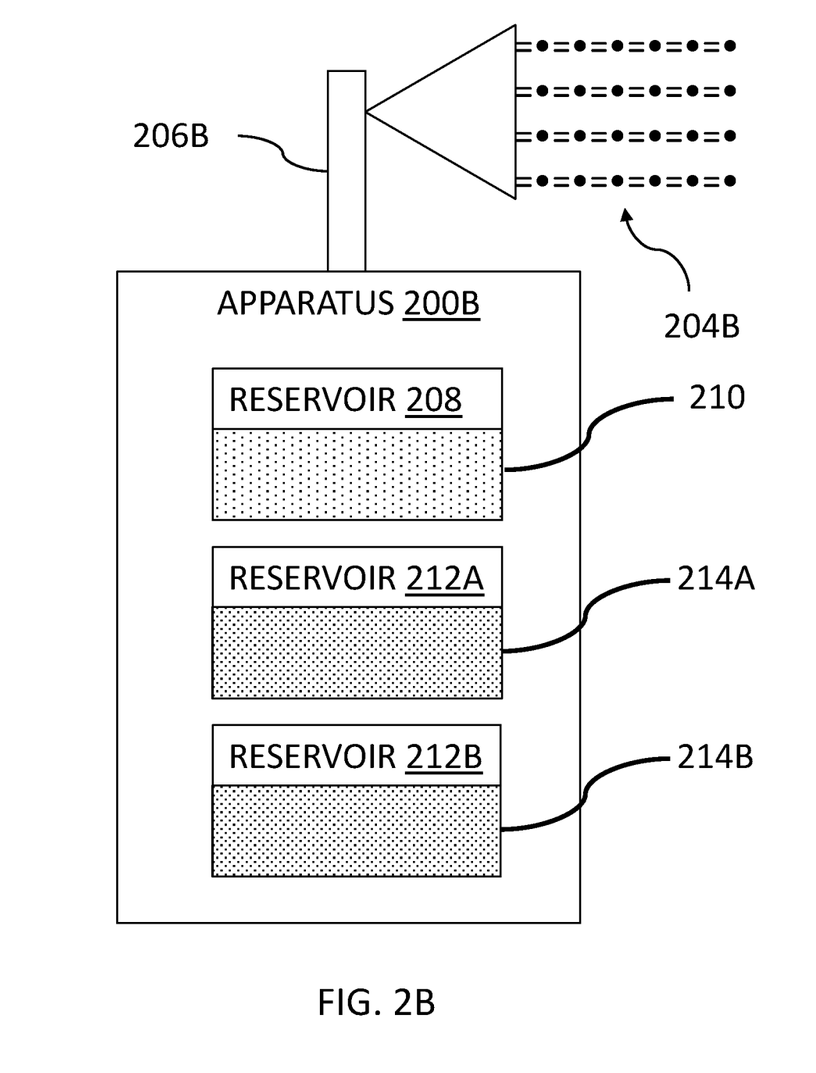

FIG. 2B illustrates another embodiment of an apparatus 200B similar to the apparatus 100 discussed with reference to FIG. 1 that can provide a mixture 204B including $N_2O$ to a subject and/or user. The apparatus 200B includes a reservoir 208 configured to store and/or storing $N_2O$ 210 and a reservoir 212A configured to store and/or storing a first additive 214A similar to various embodiments of the apparatus 200A discussed above with reference to FIG. 2A. At least in the embodiment illustrated in FIG. 2B, the apparatus 200B further includes, among other components, a reservoir 212B configured to store and/or storing a second additive 214B and a delivery mechanism 206B in communication with the reservoirs 208, 212A, and 212B and configured for introducing a mixture 204B to the nose and/or mouth of a subject.

A reservoir 212B may include any suitable reservoir and/or type of reservoir that is known or developed in the future that is capable of storing and/or housing an amount of a second additive 214B. In various embodiments, the reservoir 212B is capable of storing/housing the second additive 214B in the form of a compressed and/or pressurized liquid and/or a compressed and/or pressurized gas. As such, the second additive 214B stored in the reservoir 212B may be in the form of a compressed liquid, a pressurized liquid, a compressed gas, and/or a pressurized gas.

In some embodiments, the second additive 214B and the first additive 214A are the same additive and/or the same type of additive. In other embodiments, the second additive 214B and the first additive 214A are different additives and/or different types of additives.

The second additive 214B can include any suitable additive, substance, liquid, and/or gas that can be suitably combined with the $N_2O$ 210 (and the first additive 214A) to form a mixture 204B similar to at least one embodiment of the mixture 104 discussed above with reference to FIG. 1. For example, the second additive 214B may include, but is not limited to, air, pure oxygen, a cannabis extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206B may include any suitable device and/or system that is capable of introducing a mixture 204B including $N_2O$ 210, the first additive 214A, and the second additive 214B to the nose and/or mouth of a subject and/or user similar to the delivery mechanism 106 discussed above with reference to FIG. 1. Examples of a delivery mechanism 206B can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206B are configured to emit and/or expel the mixture 204B in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206B is configured to combine and/or facilitate combining the $N_2O$ 210 stored/housed in the reservoir 208, the first additive 214A stored/housed in the reservoir 212A, and the second additive 214B stored/housed in the reservoir 212B to generate and/or facilitate generating the mixture 204B. Since the mixture 204B includes a combination of the $N_2O$ 210, the first additive 214A, and the second additive 214B, the delivery mechanism 206B, in some embodiments, is configured to simultaneously deliver the $N_2O$ 210, the first additive 214A, and the second additive 214B to the mouth and/or nose of the subject and/or user for inhalation by the subject/user.

In various embodiments, the mixture 204B includes at least 20% of the $N_2O$ 210. That is, various embodiments of the mixture 204B can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204B, in various embodiments, includes a minimum of about 1% of the first additive 214A and the second additive 214B. That is, various embodiments of the mixture 204B can include an amount of the first additive 214A and the second additive 214B in the range of about 1% to about 80% inclusive, among other amounts and/or percentages that are less than about 1% of the first additive 214A and the second additive 214B or greater than about 80% of the first additive 214A and the second additive 214B that are possible, each of which is contemplated herein.

In some embodiments, the $N_2O$ 210, the first additive 214A, and the second additive 214B make up the entirety or substantially the entirety of the mixture 204B. In other embodiments, the $N_2O$ 210, the first additive 214A, and the second additive 214B make up less than 100% of the mixture 204B.

Figure 2C:
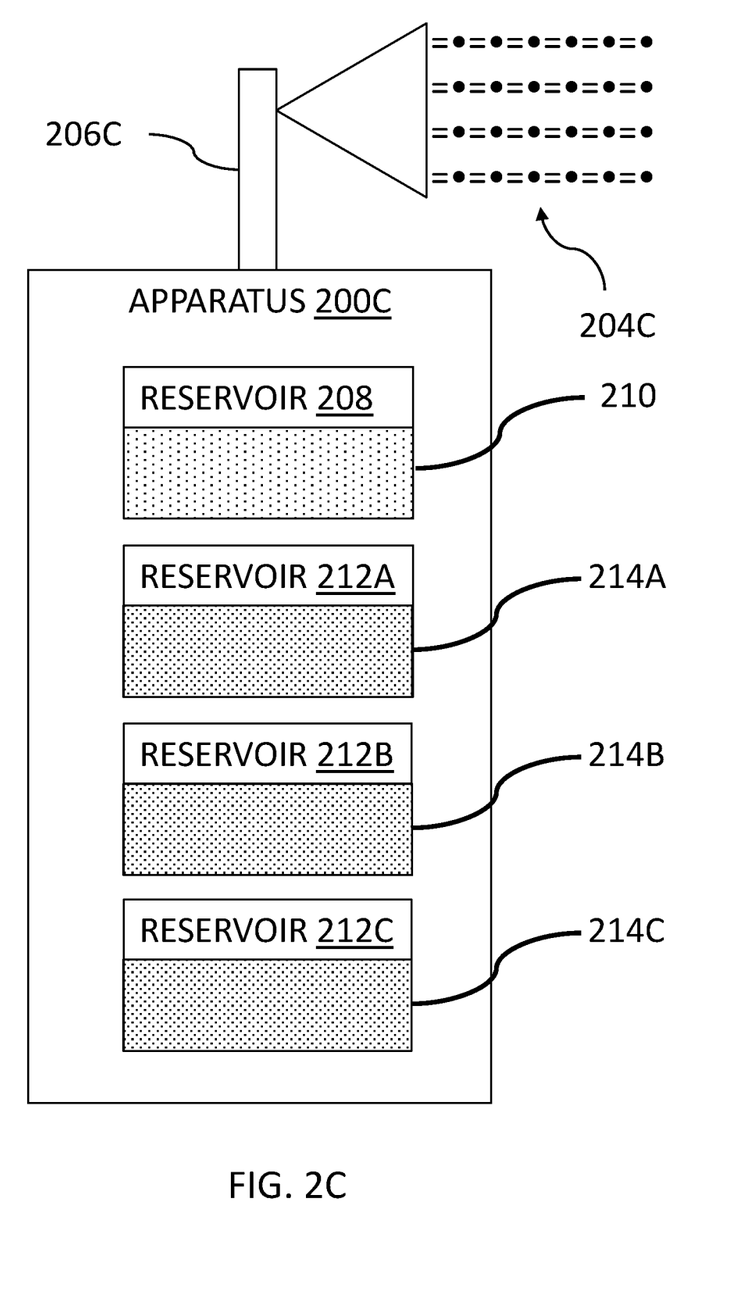

FIG. 2C illustrates a further embodiment of an apparatus 200C similar to the apparatus 100 discussed with reference to FIG. 1 that can provide a mixture 204C including $N_2O$ to a subject and/or user. The apparatus 200C includes a reservoir 208 configured to store and/or storing $N_2O$ 210, a reservoir 212A configured to store and/or storing a first additive 214A, and a reservoir 212B configured to store and/or storing a second additive 214B similar to various embodiments of the apparatus 200B discussed above with reference to FIG. 2B. At least in the embodiment illustrated in FIG. 2C, the apparatus 200C further includes, among other components, a reservoir 212C configured to store and/or storing a third additive 214C and a delivery mechanism 206C in communication with the reservoirs 208, 212A, 212B, and 212C and configured for introducing a mixture 204C to the nose and/or mouth of a subject.

A reservoir 212C may include any suitable reservoir and/or type of reservoir that is known or developed in the future that is capable of storing and/or housing an amount of a third additive 214C. In various embodiments, the reservoir 212C is capable of storing/housing the third additive 214C in the form of a compressed and/or pressurized liquid and/or a compressed and/or pressurized gas. As such, the third additive 214C stored in the reservoir 212C may be in the form of a compressed liquid, a pressurized liquid, a compressed gas, and/or a pressurized gas.

In some embodiments, the third additive 214C, the second additive 214B, and the first additive 214A are the same additive and/or the same type of additive. In other embodiments, at least two of the third additive 214C, the second additive 214B, and the first additive 214A are the same additive and/or the same type of additive. In still other embodiments, at least two of the third additive 214C, the second additive 214B, and the first additive 214A are different additives and/or different types of additives. In further embodiments, the third additive 214C, the second additive 214B, and the first additive 214A are different additives and/or different types of additives.

The third additive 214C can include any suitable additive, substance, liquid, and/or gas that can be suitably combined with the $N_2O$ 210 (and the first additive 214A and/or the second additive 214B) to form a mixture 204C similar to at least one embodiment of the mixture 104 discussed above with reference to FIG. 1. For example, the third additive 214C may include, but is not limited to, air, pure oxygen, a cannabis extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206C may include any suitable device and/or system that is capable of introducing a mixture 204C including $N_2O$ 210, the first additive 214A, the second additive 214B, and the third additive 214C to the nose and/or mouth of a subject and/or user similar to the delivery mechanism 106 discussed above with reference to FIG. 1. Examples of a delivery mechanism 206C can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206C are configured to emit and/or expel the mixture 204C in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206C is configured to combine and/or facilitate combining the $N_2O$ 210 stored/housed in the reservoir 208, the first additive 214A stored/housed in the reservoir 212A, the second additive 214B stored/housed in the reservoir 212B, and the third additive 214C stored/housed in the reservoir 212C to generate and/or facilitate generating the mixture 204C. Since the mixture 204C includes a combination of the $N_2O$ 210, the first additive 214A, the second additive 214B, and the third additive 214C, the delivery mechanism 206C, in some embodiments, is configured to simultaneously deliver the $N_2O$ 210, the first additive 214A, the second additive 214B, and the third additive 214C to the mouth and/or nose of the subject and/or user for inhalation by the subject/user.

In various embodiments, the mixture 204C includes at least 20% of the $N_2O$ 210. That is, various embodiments of the mixture 204C can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204C, in various embodiments, includes a minimum of about 1% of the first additive 214A, the second additive 214B, and the third additive 214C. That is, various embodiments of the mixture 204C can include an amount of the first additive 214A, the second additive 214B, and the third additive 214C in the range of about 1% to about 80% inclusive, among other amounts and/or percentages that are less than about 1% of the first additive 214A, the second additive 214B, and the third additive 214C or greater than about 80% of the first additive 214A, the second additive 214B, and the third additive 214C that are possible, each of which is contemplated herein.

In some embodiments, the $N_2O$ 210, the first additive 214A, the second additive 214B, and the third additive 214C make up the entirety or substantially the entirety of the mixture 204C. In other embodiments, the $N_2O$ 210, the first additive 214A, the second additive 214B, and the third additive 214C make up less than 100% of the mixture 204C.

Figure 2D:
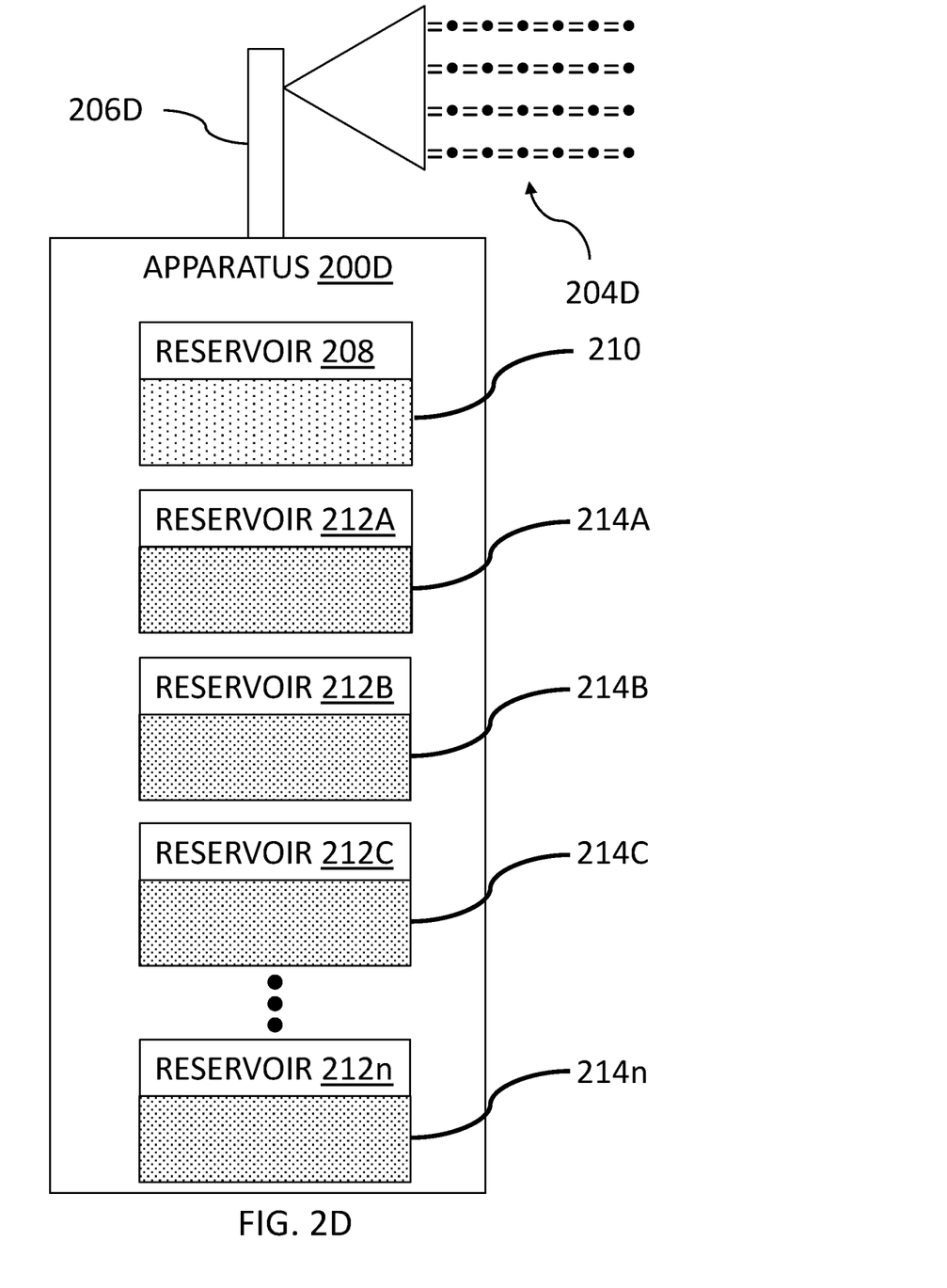

FIG. 2D illustrates a further embodiment of an apparatus 200D similar to the apparatus 100 discussed with reference to FIG. 1 that can provide a mixture 204D including $N_2O$ to a subject and/or user. The apparatus 200D includes a reservoir 208 configured to store and/or storing $N_2O$ 210, a reservoir 212A configured to store and/or storing a first additive 214A, a reservoir 212B configured to store and/or storing a second additive 214B, and a reservoir 212C configured to store and/or storing a third additive 214C similar to various embodiments of the apparatus 200C discussed above with reference to FIG. 2C. At least in the embodiment illustrated in FIG. 2D, the apparatus 200D further includes, among other components, at least one additional reservoir 212n configured to store and/or storing at least one additional additive 214n and a delivery mechanism 206D in communication with the reservoirs 208, 212A, 212B, 212C, and 212n and configured for introducing a mixture 204D to the nose and/or mouth of a subject.

A reservoir 212n may include any suitable reservoir and/or type of reservoir that is known or developed in the future that is capable of storing and/or housing an amount of a respective additional additive 214n. In various embodiments, the reservoir 212n is capable of storing/housing its respective additional additive 214n in the form of a compressed and/or pressurized liquid and/or a compressed and/or pressurized gas. As such, the additional additive 214n stored in the reservoir 212n may be in the form of a compressed liquid, a pressurized liquid, a compressed gas, and/or a pressurized gas.

In some embodiments, the additional additive 214n, the third additive 214C, the second additive 214B, and the first additive 214A are the same additive and/or the same type of additive. In other embodiments, at least two or three of the additional additive 214n, the third additive 214C, the second additive 214B, and the first additive 214A are the same additive and/or the same type of additive. In still other embodiments, at least two or three of the additional additive 214n, the third additive 214C, the second additive 214B, and the first additive 214A are different additives and/or different types of additives. In further embodiments, the additional additive 214n, the third additive 214C, the second additive 214B, and the first additive 214A are different additives and/or different types of additives.

The additional additive 214n can include any suitable additive, substance, liquid, and/or gas that can be suitably combined with the $N_2O$ 210 (and the first additive 214A, the second additive 214B, and/or the third additive 214C) to form a mixture 204D similar to at least one embodiment of the mixture 104 discussed above with reference to FIG. 1. For example, the additional additive 214n may include, but is not limited to, air, pure oxygen, a cannabis extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206D may include any suitable device and/or system that is capable of introducing a mixture 204D including $N_2O$ 210, the first additive 214A, the second additive 214B, the third additive 214C, and one or more additional additives 214n to the nose and/or mouth of a subject and/or user similar to the delivery mechanism 106 discussed above with reference to FIG. 1. Examples of a delivery mechanism 206D can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206D are configured to emit and/or expel the mixture 204D in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206D is configured to combine and/or facilitate combining the $N_2O$ 210 stored/housed in the reservoir 208, the first additive 214A stored/housed in the reservoir 212A, the second additive 214B stored/housed in the reservoir 212B, the third additive 214C stored/housed in the reservoir 212C, and each additional additive 214n stored/housed in a respective reservoir 212n to generate and/or facilitate generating the mixture 204D. Since the mixture 204D includes a combination of the $N_2O$ 210, the first additive 214A, the second additive 214B, the third additive 214C, and one or more additional additives 214n, the delivery mechanism 206D, in some embodiments, is configured to simultaneously deliver the $N_2O$ 210, the first additive 214A, the second additive 214B, the third additive 214C, and each additional additive 214n to the mouth and/or nose of the subject and/or user for inhalation by the subject/user.

In various embodiments, the mixture 204D includes at least 20% of the $N_2O$ 210. That is, various embodiments of the mixture 204D can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204D, in various embodiments, includes a minimum of about 1% of the first additive 214A, the second additive 214B, the third additive 214C, and each additional additive 214n. That is, various embodiments of the mixture 204D can include an amount of the first additive 214A, the second additive 214B, the third additive 214C, and each additional additive 214n in the range of about 1% to about 80% inclusive, among other amounts and/or percentages that are less than about 1% of the first additive 214A, the second additive 214B, the third additive 214C, and each additional additive 214n or greater than about 80% of the first additive 214A, the second additive 214B, the third additive 214C, and each additional additive 214n that are possible, each of which is contemplated herein.

In some embodiments, the $N_2O$ 210, the first additive 214A, the second additive 214B, the third additive 214C, and each additional additive 214n make up the entirety or substantially the entirety of the mixture 204D. In other embodiments, the $N_2O$ 210, the first additive 214A, the second additive 214B, the third additive 214C, and each additional additive 214n make up less than 100% of the mixture 204C.

Figure 3:
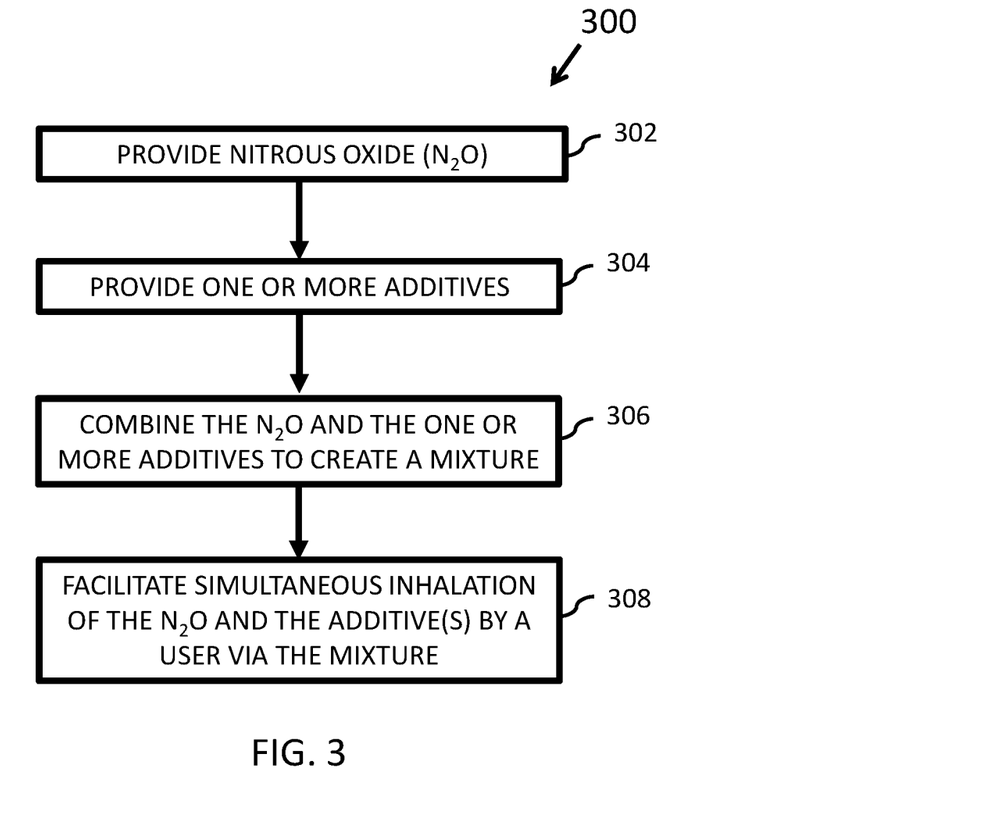
FIG. 3 is a schematic flow diagram of one embodiment of a method for provide a mixture including nitrous oxide $N_2O$ to a subject/user.

FIG. 3 is a schematic flow diagram of one embodiment of a method 300 that can provide a mixture (e.g., mixture 104 or mixture(s) 204) including $N_2O$ to a subject/user. At least in the illustrated embodiment, the method 300 begins by providing $N_2O$ (block 302), providing one or more additives (e.g., additives 214A, 214B, 214C, and 214n, hereinafter referred to singularly or collectively simply as, additive(s) 214) (block 304), and combine the $N_2O$ and the additive(s) to form a mixture 104/204 including $N_2O$ and one or more additives (block 306).

In some embodiments, the mixture 104/204 includes at least 20% $N_2O$. In certain embodiments, the mixture 104/204 can include an amount of $N_2O$ in the range of about 20% to about 99% inclusive, among other amounts and/or percentages that are less than about 20% $N_2O$ or greater than about 99% $N_2O$ that are possible, each of which is contemplated herein.

The mixture 104/204 can include any suitable quantity of additives 214. In various embodiments, the mixture 104/204 includes one additive 214, two additives 214, three additives 214, four additives 214, or five additives 214, among other quantities that are greater than five additives 214, each of which is contemplated herein.

The mixture 104/204, in various embodiments, includes a minimum of about 1% of the additive(s) 214. That is, various embodiments of the mixture 104/204 can include an amount of the additive(s) 214 in the range of about 1% to about 80% inclusive, among other amounts and/or percentages that are less than about 1% of the additive(s) 214 or greater than about 80% of the additive(s) 214 that are possible, each of which is contemplated herein.

The method 300 further includes facilitating simultaneous inhalation of the $N_2O$ and the additive(s) by a user (block 308). In various embodiments, the simultaneous inhalation of the $N_2O$ and the additive(s) by the user is facilitated by a delivery mechanism (e.g., delivery mechanism 106, 206A, 206B, 206C, and 206D).

As discussed above, since a mixture 104/204 includes a combination of $N_2O$ and one or more additives, the delivery mechanism 106 is capable of simultaneously delivering the $N_2O$ and the one or more additives to the mouth and/or nose of a subject (e.g., a user) for inhalation by the subject/user.

Reference throughout this specification to one embodiment, an embodiment, or similar language means that a particular feature, structure, or characteristic described in connection with the embodiment is included in at least one embodiment. Thus, appearances of the phrases in one embodiment, in an embodiment, and similar language throughout this specification may, but do not necessarily, all refer to the same embodiment, but mean one or more but not all embodiments unless expressly specified otherwise. The terms including, comprising, having, and variations thereof mean including but not limited to, unless expressly specified otherwise. An enumerated listing of items does not imply that any or all of the items are mutually exclusive, unless expressly specified otherwise. The terms, "a," "an," and "the," also refer to one or more unless expressly specified otherwise.

In addition, as used herein, the term, "set," can mean one or more, unless expressly specified otherwise. The term, "sets," can mean multiples of or a plurality of one or mores, ones or more, and/or ones or mores consistent with set theory, unless expressly specified otherwise.

Furthermore, the described features, structures, or characteristics of the embodiments may be combined in any suitable manner. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

It should also be noted that, in some alternative implementations, the functions noted in the block may occur out of the order noted in the Figures. For example, two blocks shown in succession may, in fact, be performed substantially concurrently, or the blocks may sometimes be performed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment.

The description of elements in each figure may refer to elements of proceeding figures. Like numbers refer to like elements in all figures, including alternate embodiments of like elements.

The various disclosed embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus, comprising:
a first reservoir storing at least nitrous oxide ($N_2O$);
a second reservoir storing at least a first non-oxygen additive that is different than $N_2O$; and
a sprayer in communication with the first reservoir and the second reservoir and, upon actuation of the sprayer, is configured to:
combine the $N_2O$ and the first additive to create a mixture, and
introduce the mixture to a mouth of a subject for inhalation by the subject to inhibit N-methyl-D-aspartate (NMDA) receptors of the subject,
wherein:
the mixture comprises a first amount of $N_2O$ that is greater than 25% and less than 50% of the mixture,
the mixture comprises a second amount of the first non-oxygen additive that is greater than 50% and less than 75% of the mixture, and
the apparatus is a portable handheld inhaler.

2. The apparatus of claim 1, wherein:
at least one of the first reservoir and the second reservoir further stores a second additive that is different than the $N_2O$ and the first non-oxygen additive; and
the mixture further comprises the second additive combined with the $N_2O$ and the first non-oxygen additive.

3. The apparatus of claim 2, wherein:
the first non-oxygen additive comprises one of water and hydrogen peroxide ($H_2O_2$); and
the second additive comprises one of compressed air, pure oxygen ($O_2$), air, and atmospheric air.

4. The apparatus of claim 1, wherein the first non-oxygen additive comprises a cannabis extract.

5. The apparatus of claim 1, wherein the first non-oxygen additive comprises one of an essential oil, an herbal extract, a supplement, a medication, a vitamin, and a nutrient.

6. The apparatus of claim 1, wherein the first non-oxygen additive comprises caffeine.

7. The apparatus of claim 1, wherein the first non-oxygen additive comprises one of a colloidal silver and a nano-silver.

8. The apparatus of claim 1, wherein the first non-oxygen additive comprises a nano-capacitor.

9. The apparatus of claim 1, wherein:
the first reservoir stores a single-use quantity of the $N_2O$;
the second reservoir stores a single-use quantity of the first non-oxygen additive; and
actuation of the sprayer creates a single-use quantity of the mixture of the $N_2O$ and the first non-oxygen additive.

10. The apparatus of claim 1, wherein:
the first reservoir stores a multi-use quantity of the $N_2O$;
the second reservoir stores a multi-use quantity of the first non-oxygen additive; and
each actuation of the sprayer creates a single-use quantity of the mixture of the $N_2O$ and the first non-oxygen additive.

11. An apparatus, comprising:
a first reservoir storing at least nitrous oxide ($N_2O$);
a second reservoir storing at least a first non-oxygen additive that is different than $N_2O$; and
a delivery mechanism in communication with the first reservoir and the second reservoir and, upon actuation of the delivery mechanism, is configured to:
combine the $N_2O$ and the first non-oxygen additive to create a mixture, and
introduce the mixture to a subject for inhalation by the subject to inhibit N-methyl-D-aspartate (NMDA) receptors of the subject,
wherein:
the mixture comprises a first amount of $N_2O$ that is greater than 25% and less than 50% of the mixture,
the mixture comprises a second amount of the first non-oxygen additive that is greater than 50% and less than 75% of the mixture, and
the delivery mechanism comprises a portable nebulizer.

12. The apparatus of claim 11, wherein:
at least one of the first reservoir and the second reservoir further stores a second additive that is different than the $N_2O$ and the first non-oxygen additive; and the mixture further comprises the second additive combined with the $N_2O$ and the first non-oxygen additive.

13. The apparatus of claim 12, wherein:
the first non-oxygen additive comprises one of water and hydrogen peroxide ($H_2O_2$); and
the second additive comprises one of compressed air, pure oxygen ($O_2$), air, and atmospheric air.

14. The apparatus of claim 11, wherein the first non-oxygen additive comprises a cannabis extract.

15. The apparatus of claim 11, wherein the first non-oxygen additive comprises one of an essential oil, an herbal extract, a supplement, a medication, a vitamin, and a nutrient.

16. The apparatus of claim 11, wherein the first non-oxygen additive comprises caffeine.

17. The apparatus of claim 11, wherein the first non-oxygen additive comprises one of a colloidal silver and a nano-silver.

18. The apparatus of claim 11, wherein the first non-oxygen additive comprises a nano-capacitor.

19. The apparatus of claim 11, wherein:
the first reservoir stores a single-use quantity of the $N_2O$;
the second reservoir stores a single-use quantity of the first non-oxygen additive; and
actuation of the delivery mechanism creates a single-use quantity of the mixture of the $N_2O$ and the first non-oxygen additive.

20. The apparatus of claim 11, wherein:
the first reservoir stores a multi-use quantity of the $N_2O$;
the second reservoir stores a multi-use quantity of the first non-oxygen additive; and
each actuation of the delivery mechanism creates a single-use quantity of the mixture of the $N_2O$ and the first non-oxygen additive.

\* \* \* \* \*